US008647252B2

(12) United States Patent
Diament (10) Patent No.: US 8,647,252 B2
(45) Date of Patent: Feb. 11, 2014

(54) APPLYING TORQUE TO PARAMAGNETIC STRUCTURES IN BODIES USING DUAL MAGNETIC FIELDS

(75) Inventor: Paul Diament, New Rochelle, NY (US)

(73) Assignee: The Trustees of Columbia University in the City of New York

( * ) Notice: Subject to any disclaimer, the term of this patent is extended or adjusted under 35 U.S.C. 154(b) by 267 days.

(21) Appl. No.: 13/129,453

(22) PCT Filed: Nov. 13, 2009

(86) PCT No.: PCT/US2009/064473
§ 371 (c)(1),
(2), (4) Date: Jul. 12, 2011

(87) PCT Pub. No.: WO2010/057050
PCT Pub. Date: May 20, 2010

(65) Prior Publication Data
US 2012/0130149 A1     May 24, 2012

Related U.S. Application Data

(60) Provisional application No. 61/114,999, filed on Nov. 14, 2008.

(51) Int. Cl.
*A61N 2/00*     (2006.01)
(52) U.S. Cl.
USPC .................................. 600/12; 600/9

(58) Field of Classification Search
USPC ................ 600/9–15; 604/20; 607/1, 5, 45, 48
See application file for complete search history.

(56) References Cited

U.S. PATENT DOCUMENTS

| 5,572,124 | A | 11/1996 | Bito et al. |
| 7,326,170 | B1 | 2/2008 | Miller |
| 2003/0201208 | A1 | 10/2003 | Koch et al. |
| 2006/0009826 | A1* | 1/2006 | Gleich ............... 607/103 |
| 2006/0142749 | A1* | 6/2006 | Ivkov ................ 606/27 |
| 2007/0196281 | A1* | 8/2007 | Jin et al. ............ 424/9.34 |

OTHER PUBLICATIONS

Blaine R. Copenheaver, "WO2010/057050 International Search Report Written Opinion", Jan. 20, 2010.

* cited by examiner

*Primary Examiner* — Christine Matthews
*Assistant Examiner* — Laura Fajardo (57) ABSTRACT

Techniques for applying torque to microscopic paramagnetic structures in a body includes exposing a body simultaneously to a first magnetic field oscillating at a first frequency in a first direction and a different second magnetic field oscillating at a second frequency in a second direction. The body includes a plurality of microscopic paramagnetic structures for which magnetic susceptibility to the first magnetic field is different from magnetic susceptibility to the second magnetic field. Such techniques are effective for ameliorating a symptom of a disease in an animal in which disease agents or diseased cells selectively include microscopic paramagnetic structures, including malaria.

14 Claims, 10 Drawing Sheets

APPLYING TORQUE TO PARAMAGNETIC STRUCTURES IN BODIES USING DUAL MAGNETIC FIELDS

CROSS-REFERENCE TO RELATED APPLICATIONS

This application claims benefit of Provisional Appln. 61/114,999, filed Nov. 14, 2008, the entire contents of which are hereby incorporated by reference as if fully set forth herein, under 35 U.S.C. §119(e).

BACKGROUND OF THE INVENTION

1. Field of the Invention

The present invention relates to treating conditions in a body by applying torque to microscopic paramagnetic structures in the body to excite mechanical motion of those structures.

2. Description of the Related Art

Malaria affects millions of people all over the world. Upon infecting a red blood cell, the malaria parasite feeds on hemoglobin (Hb) and breaks the Hb down inside a food vacuole in the parasite. The heme part of Hb is called ferritoprotoporphin IX (abbreviated as Fe(III)PPIX); and cannot be digested by the parasite. The parasite transforms the Fe(III)PPIX into crystalline stacks called hemozoin. Hemozoin is a crystalline dimer of Fe(III)PPIX with a well defined crystalline structure which can be described as lath-like. These crystals in the vacuole of the parasite are typically close to 1 micron ($\mu m$, 1 $\mu m = 10^{-6}$ meters) in length and several hundred nanometers (nm, 1 $nm = 10^{-9}$ meters) in width. The magnetic susceptibility of hemozoin varies depending on the nature of the solution in which it is found; but, the resulting magnetic moment is generally within 1 to 5 Bohr magneton, which makes hemozoin super-paramagnetic. Magnetic susceptibility indicates the tendency of magnetic dipoles in a material to align in response to an externally applied magnetic field. The resulting alignment causes the material to behave as a small magnet that experiences a force depending on the magnet's orientation relative to the externally applied magnetic field.

Low frequency oscillating magnetic fields have been shown to cause mechanical torsion of hemozoin within red blood cells infected by the malaria parasite (J. E. Feagan, M. A. W. Wurscher, C. Ramon, H. Lai, "Magnetic fields and Malaria," *Biologic Effects of Light: Proceedings of the Biologic Effects of Light Symposium*, Hlick, M. F. and Jung, E. G. Kluwer Academic Publishers, Hingham, M A, pp 343-349, 1999). According to Feagan et al., the mechanical torsion is sufficient to cause membrane disruption inside the parasite cell and hence the destruction of the parasite. Alternatively, the authors suggested that beside mechanical disruption of parasitic membranes, the applied magnetic field also inhibited the biopolymerization of heme, thus imposing the toxic effect of heme on the parasite and causing its death. After 24 hour exposure to an alternating magnetic field of 15 Gauss (Gs) at 5 cycles per second (Hertz, Hz) the level of parasite in culture was reduced to a range from about 70% to about 33% of the level in untreated control samples.

SUMMARY OF THE INVENTION

Techniques are provided for applying torque to microscopic paramagnetic structures in a body that offer advantages over prior art approaches.

In a first set of embodiments, a method includes exposing a body simultaneously to a first magnetic field oscillating at a first frequency in a first direction and a different second magnetic field oscillating at a second frequency in a second direction. The body includes a plurality of microscopic paramagnetic structures for which magnetic susceptibility to the first magnetic field is different from magnetic susceptibility to the second magnetic field.

In another set of embodiments, a method ameliorates a symptom of a disease in an animal (including mammals, humans and laboratory animals) for which disease agents or diseased cells selectively include microscopic paramagnetic structures. The method includes exposing the animal to a therapeutically effective strength and duration of a first magnetic field oscillating at a first frequency in a first direction and, simultaneously, a different second magnetic field oscillating at a second frequency in a second direction.

In another set of embodiments, an apparatus includes a first magnet adapted to generate a first magnetic field oscillating at a first frequency in a first direction. Also included is a second magnet adapted to generate a different second magnetic field oscillating at a second frequency in a second direction. A patient treatment platform is adapted to position a patient simultaneously in the first magnetic field and the second magnetic field. The first frequency and the second frequency are selected so that magnetic susceptibility for microscopic paramagnetic structures associated with a condition in the patient is different in the first magnetic field than in the second magnetic field.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Methods and apparatus are described for applying torque to microscopic paramagnetic structures in a body. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of certain life cycle stages of the malaria parasite. However, the invention is not limited to this context. In other embodiments the invention is applied to other diseases involving hemozoin and other paramagnetic structures. For example, other diseases involving hemozoin include other blood-feeding organisms, such as helminth worms *Schistosoma mansoni* (the causative agent of schistosomiasis or bilharzias), *Echinostoma trivolvis*, bird-infecting protozoan *Haemoproteus columbae*, and the parasite *Trypanosoma cruzi*, which causes Chagas disease (American trypanosomiasis). Other diseases similarly associated with the accumulation of paramagnetic or ferromagnetic products in infected cells include tuberculosis and toxoplasmosis, among others. As used herein, a list following the term "including" (or "comprising") is not intended to be comprehensive and any other members not listed are intended.

1. Overview

Figure 1A:
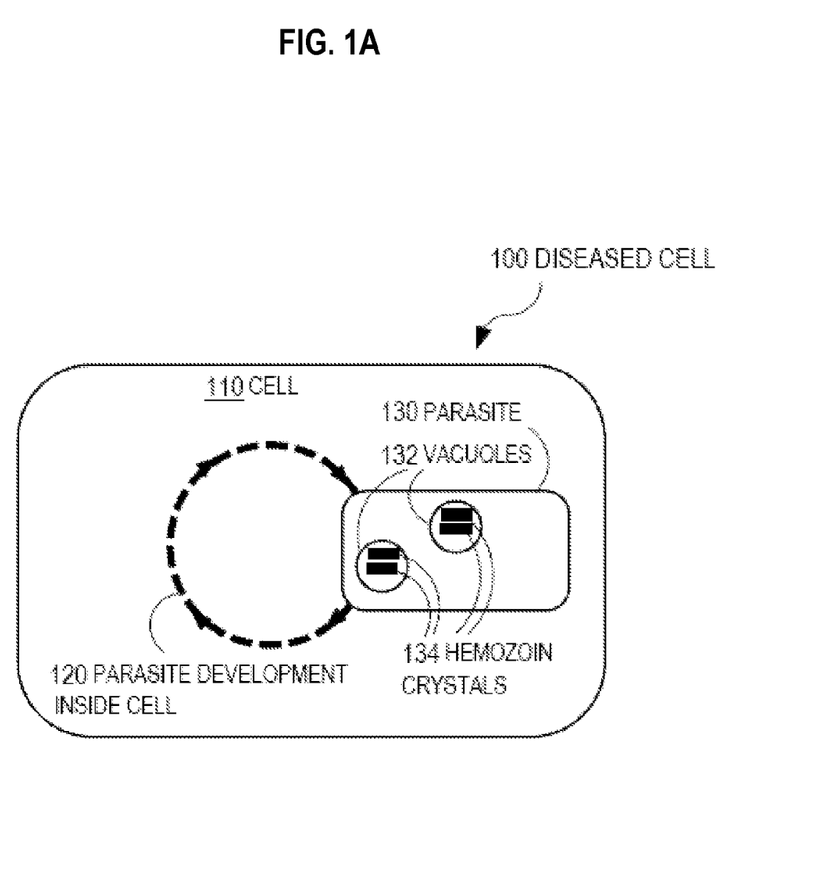
FIG. 1A is a block diagram that illustrates a diseased cell with microscopic paramagnetic structures.

Malaria remains a virulent scourge in many parts of the world. The parasite invades red blood cells, feeds on the hemoglobin and accumulates hemozoin, an iron crystal, which remains within the parasite in the host cell. FIG. 1A is a block diagram that illustrates a diseased cell 110 with microscopic paramagnetic structures, as in a malaria parasite. The cell 110 includes a parasite 130 that develops during one or more stages in the cell, represented by cycle 120. In the illustrated stage, the parasite 130 includes one vacuole 132 that includes several hemozoin crystals 134 (typically 3 to 5 and up to ten). By forming the hemozoin 134 in the vacuoles 132, the parasite 130 is protected from toxic effects of the heme. Hemozoin crystals 134 are one example of microscopic paramagnetic structures composed of multiple atoms and molecules and selectively included in disease agents or diseased cells. As used herein, a microscopic structure is one in the size range from about 0.01 micron to about 100 microns.

Figure 1B:
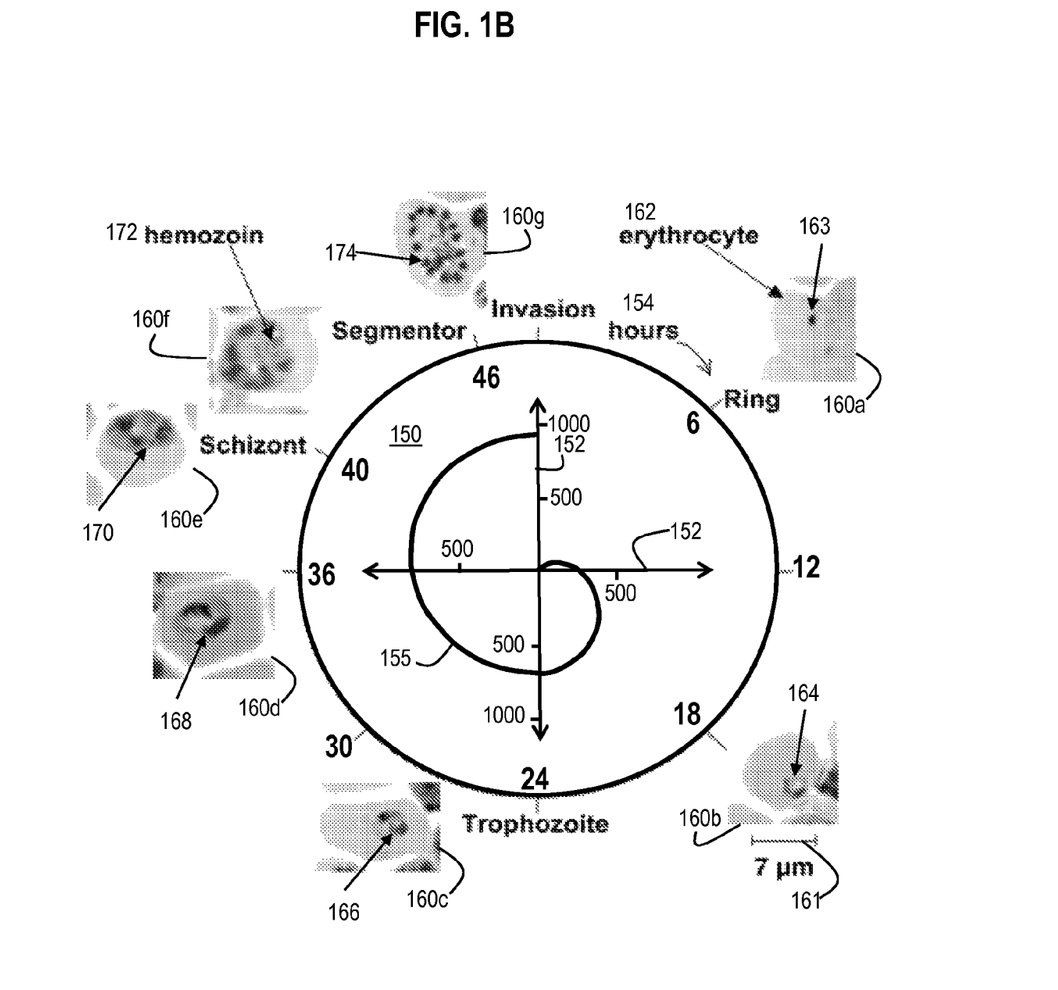
FIG. 1B is a block diagram that illustrates several phases of diseased cells with microscopic paramagnetic structures.

FIG. 1B is a block diagram that illustrates several phases of diseased cells with microscopic paramagnetic structures during a 48 hour disease cycle. The diagram includes a polar coordinate graph 150 and seven micrograph images 160a through 160g. The radial axis 152 of the polar coordinate graph 150 indicates the hemozoin content in picoMoles (pmol, 1 pmol=$10^{-12}$ Moles) per million infected red blood cells (RBC). The azimuthal angle 154 from the top of the graph indicates the time in hours after invasion. In the 46 to 48 hour cycle of the malaria parasite, the hemozoin content rises from zero to almost 1000 pmol per million infected RBC as shown by trace 155. Micrographs 160a through 160g depict example infected RBC at several stages on a spatial scale given by bar 161 that represents seven microns (7 μm).

Malaria is a parasite-borne disease that infects about 650 million people and causes nearly three million deaths a year. The most common form of malaria is caused by the parasite *Plasmodium falciparum* (Pf) which infects a red blood cell (RBC, also called an erythrocyte). The Pf life cycle proceeds through several asexual and sexual stages. *Plasmodium* sporozoites, transmitted by female *Anopheles* mosquitoes, are injected into the blood of an animal host together with mosquito saliva. After initial proliferation in the liver, parasites in the merozoite stage are released back into the blood stream. A single merozoite then invades a RBC and matures while deforming the RBC into a ring-shape after about 6 hours. Micrograph 160a depicts a RBC (erythrocyte) infected by a single merozoite 163. In about 24 hours the matured parasite enters the trophozoite stage, during which most of the RBC cytoplasm, including hemoglobin, is catabolized, i.e., complex substances in the RBC are converted by the parasite into more simple compounds, accompanied by a release of energy. This stage is depicted by micrograph 160c and 160d and 160e, showing progressive catabolization of RBC cytoplasm 166 and 168 and 170, respectively. Through the final (schizont) stage in the RBC, after about 40 hours, the parasite undergoes several divisions, depicted in micrographs 160f and 160g to produce up to thirty-two new merozoites 174 that, during the segmentor stage at about 46 hours, burst the host RBC and invade up to 32 new RBCs.

Hemozoin crystals 172 are present in their largest quantities during the schizont stage. In fact hemozoin content is near its maximum value even at the start of the trophozoite stage, indicating the most vulnerable stages for targeting hemozoin are in the trophozoite and schizont stages, i.e. the III and IV quarters of a 48 h cycle.

Applicants have determined, as explained in more detail below, that previous approaches (e.g., Feagan et al., cited above) are not able to induce more than a subtle drift or damped vibration in the hemozoin crystals 134 and 172.

Applicants have further determined that applying a mechanical torque to the hemozoin crystals 134 in malaria and other parasites will cause the crystal to move more vigorously, such as by rotating, oscillating, agitating, vibrating, or churning, alone or in some combination. Such vigorous motion should achieve more effective destruction of the parasite than prior art approaches, either directly by mechanical battery that can tear the parasite's internal membranes, causing release of digestive enzymes into parasite cytoplasm which will eventually cause autolysis, or indirectly by conversion of the mechanical energy into heat. The torque is to be applied by suitable magnetic fields, different from the single 5 Hz and 15 Gs oscillating magnetic fields disclosed in the prior art.

The following analysis demonstrates that it is advantageous to use two distinct magnetic susceptibilities of the crystal to induce a torque.

2. Analysis of Magnetic Field Induced Torque on Paramagnetic Structures

The following analysis is presented to provide a more detailed understanding of embodiments of the invention so that others can make and use it and appreciate the advantages. However the invention is not limited by the accuracy or completeness of the following analysis.

Figure 2A:
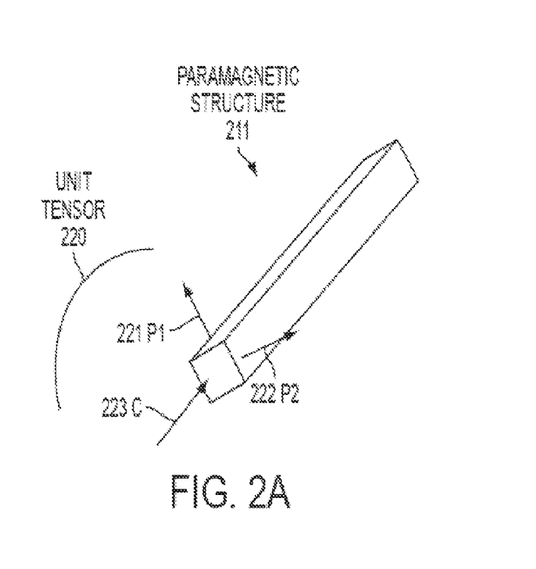
FIG. 2A, FIG. 2B and FIG. 2C are block diagrams that illustrate example microscopic paramagnetic structures suitable as targets for various embodiments of the invention.
Figure 2B:
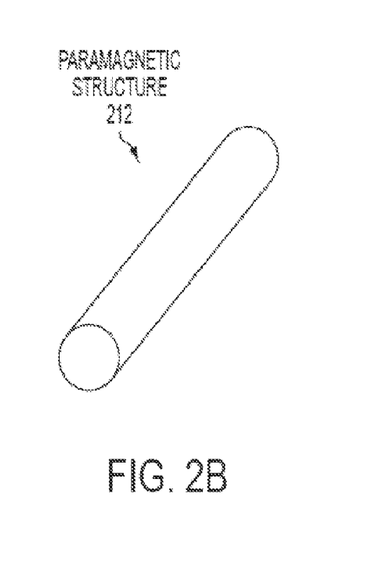
Figure 2C:
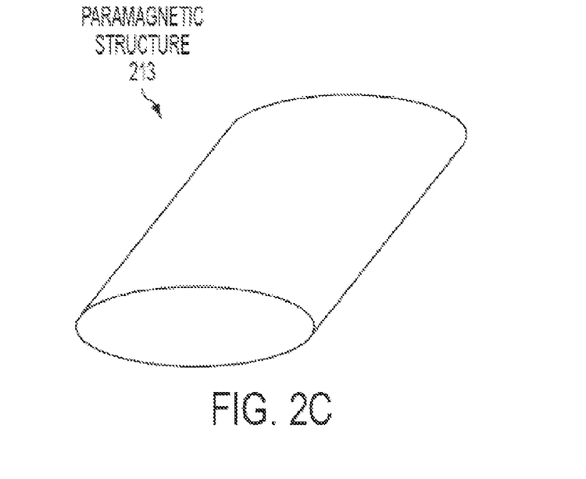

FIG. 2A, FIG. 2B and FIG. 2C are block diagrams that illustrate example microscopic paramagnetic structures suitable as targets of various embodiments of the invention. FIG. 2A illustrates an elongated paramagnetic structure 211 with a polygonal face. A quadrilateral face is illustrated. The spatial orientation is expressed by a unit vector c 223, which has a magnitude equal to 1 and a direction aligned with the longitudinal axis of the structure 211. The unit vector c has three components for the three dimensions in the macroscopic reference frame (e.g., the reference frame of a patient, laboratory or externally applied magnetic field). Two perpendicular unit vectors p1 221 and p2 222 indicate the transverse directions perpendicular to the unit vector c. The three unit vectors c, p1 and p2 can be combined as one way of representing the unit tensor 220. A tensor is essentially a vector of vectors. Symbols representing vectors and tensors are presented in bold typeface, herein.

The behavior of the paramagnetic structure may be represented by a tensor in which the components express the relative strengths of the response to stimuli along the three spatial directions. The inertia of the paramagnetic structure, dependent on the distribution of mass within the structure, is given by the tensor J; and the magnetic susceptibility by the tensor $\chi$.

Figure 3:
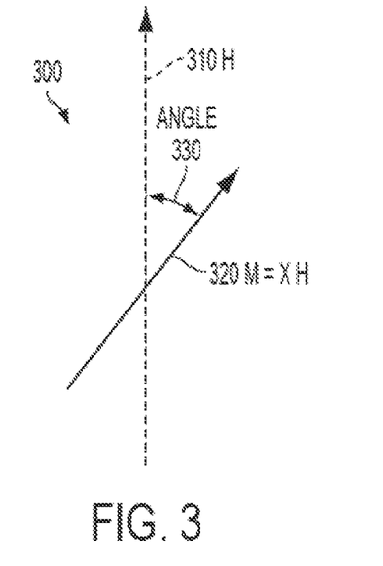
FIG. 3 is a block diagram that illustrates spatial relationships between microscopic paramagnetic structures and an externally applied magnetic field.

Magnetic susceptibility $\chi$ is defined by Equation 1 and determined by experiment.

$$M = \chi H \quad (1)$$

where H is the intensity of the externally applied magnetic field (a vector) and M is the resulting magnetic moment per unit volume (also a vector). If the crystal is isotropic, i.e., is able to align all magnetic dipoles with the external field, then $\chi$ is a scalar, and M is parallel to H. Otherwise, the structure is said to be anisotropic, and $\chi$ is a tensor that converts the vector H to the vector M by the rules of tensor multiplication. FIG. 3 is a block diagram 300 that illustrates spatial relationships between microscopic paramagnetic structures and an externally applied magnetic field for an anisotropic magnetic susceptibility. FIG. 3 depicts the externally applied magnetic field H 310 in one direction, and the resulting M 320 in a different direction at an angle 330 from H.

FIG. 2B illustrates a slightly different elongated paramagnetic structure 212 with a circular face. This structure exhibits rotational symmetry about the longitudinal axis, and is well described with a single transverse tensor component. Thus the analysis of structure 212 is mathematically simpler than that of structure 211. However, because the structure 211 is so similar to structure 212, the simpler analysis for structure 212 should closely approximate the results of a more complex analysis for structure 211. FIG. 2C illustrates a different elongated paramagnetic structure 213 with an oval face. This structure 213 is significantly elongated in both the longitudinal direction and one of the perpendicular directions. Not shown is a spherical structure, which is well described by scalar quantities. In the following analysis, the paramagnetic structure 212, which is sufficiently similar to the structure of hemozoin, is often used as an illustration.

2.1. Torque Depends on Differences in Magnetic Susceptibility.

Magnetically induced torque dT on the contents of an infinitesimal volume dV is given by Equation 2.

$$dT = M \times B \, dV \quad (2)$$

where B is the magnetic flux density and M is the magnetic moment per unit volume at the location of dV.

If the applied field is reasonably uniform over the volume of the hemozoin and as the environment differs negligibly in its magnetic properties from a nonmagnetic substance, the magnetic flux density B is related to the applied field H by Equation 3.

$$B = \mu_0 H \quad (3)$$

where $\mu_0$ is the permeability of free space. Then the total torque applied to the target volume V is given by Equation 4.

$$T = \mu_0 V \chi H \times H \quad (4)$$

Because the cross product of any vector with itself vanishes, we see immediately that, if the susceptibility is a scalar, a single magnetic field will not result in a torque. There may be drift, but there won't be the vigorous motion provided by torque. It is desirable to have no less than two non-zero susceptibilities in a susceptibility tensor so that torque can be generated.

2.2. Multiple Frequencies for Isotropic Susceptibility.

Magnetic susceptibility is a function of angular frequency w of the externally applied field. If anisotropy of the crystal is absent or insufficient, a magnetic field that oscillates at two distinct frequencies can be used to generate torque. In these embodiments, the total magnetic field is given by Equation 5a and the corresponding magnetic moment is given by Equation 5b. It is assumed for purposes of illustration that susceptibility is a scalar at both frequencies, i.e., the material is isotropic or insufficiently anisotropic.

$$H = H_1 + H_2 \quad (5a)$$

$$M = \chi_1 H_1 + \chi_2 H_2, \quad (5b)$$

so that the torque is given by Equation 6c (derived from Equation 6a as shown).

$$T = \mu_0 V (\chi_1 H_1 + \chi_2 H_2) \times (H_1 + H_2) \quad (6a)$$

$$= \mu_0 V [(\chi_1 H_1 + H_2) + (\chi_2 H_2 \times H_1)] \quad (6b)$$

$$= \mu_0 V (\chi_1 - \chi_2) H_1 \times H_2 \quad (6c)$$

Clearly, scalar susceptibilities at the two frequencies must be distinct and preferably significantly different; and the magnetic fields at the two frequencies must not be oriented parallel to each other (preferably they are oriented perpendicular to each other to maximize the torque resulting from the applied fields $H_1$ and $H_2$).

For purposes of illustration, it is assumed that the two frequencies are $\omega_1$ and $\omega_2$, and the two fields are given by Equation 7a and 7b.

$$H_1(t) = H_{01} \cos \omega_1 t \quad (7a)$$

$$H_2(t) = H_{02} \cos(\omega_2 + \theta) \quad (7b)$$

where the amplitudes $H_{01}$, $H_{02}$ are constants in time and $\theta$ is the initial phase difference between the two fields. The resulting torque is given by Equation 8a (or Equation 8b) . . .

$$T(t) = \mu_0 V (\chi_1 - \chi_2) H_{01} \times H_{02} \cos(\omega_1 t) \cos(\omega_2 t + \theta) \quad (8a)$$

$$= \frac{1}{2} \mu_0 V \Delta \chi H_{01} \times H_{02} \cos([\omega_1 + \omega_2]t + \theta) + \quad (8b)$$

$$\frac{1}{2} \mu_0 V \Delta \chi H_{01} \times H_{02} \cos([\omega_1 - \omega_2]t - \theta)$$

where $\Delta\chi = \chi_1 - \chi_2$ is the difference between the susceptibilities at the two frequencies.

The angular velocity of the crystal in response to this torque is derived from the equation of motion given by Equation 9.

$$T = d(J \cdot \omega)/dt \quad (9)$$

where $\omega$ is the angular velocity vector (pointed perpendicular to the plane in which the structure rotates). Recall J relates to the distribution of mass in the crystal. Assuming the crystal is initially not rotating, the angular momentum at time t is the integral of the torque, as given by Equations 10a through 10d.

$$J(t) \cdot \omega(t) = L_0 f(t) \quad (10a)$$

where $$f(t) = \sin([\omega_1 - \omega_2]t - \theta) + \xi \sin([\omega_1 + \omega_2]t + \theta) + (1 - \xi) \sin \theta \quad (10b)$$

$$L_0 = \tfrac{1}{2}\mu_0 V(\chi_1-\chi_2)(H_{01} \times H_{02})/(\omega_1-\omega_2) \quad (10c)$$

$$\xi = (\omega_1-\omega_2)/(\omega_1+\omega_2) \quad (10d)$$

The difference-frequency term, $\sin([\omega_1-\omega_2]t-\theta)$, will be the dominant one in the angular velocity in many embodiments, especially if the two frequencies are relatively high but close to each other.

To separate the terms $J(t)$ and $\omega(t)$ from the product given in Equation 10a, it is assumed for purposes of illustration that the crystal is uni-axial (e.g., like structure 211 or structure 212). In this embodiment, the inertia tensor J can be expressed in terms of the components of the unit tensor, as given by Equation 11a or 11b.

$$J = \alpha cc + \beta(1-cc) \quad (11a)$$

$$= \beta 1 + (\alpha-\beta)cc \quad (11b)$$

where cc is a tensor resulting from the outer product of the unit vector c 223 with itself, c is a function of time (expressed as c(t)) that indicates motion of the crystal, and 1 is the unit tensor 220. This J describes moments of inertia equal to $\alpha$ longitudinally and $\beta$ transversely. The motion of the crystal is given by the changes in the unit vector c 223 with time.

For purposes of illustration, the crystal is treated as a rigid body and the motion of the crystal is given by Equation 12.

$$dc/dt = \omega \times c \quad (12)$$

which indicates precession of c around $\omega$, which itself oscillates.

With these substitutions, Equation 10 becomes $$J \cdot \omega = L_0 f(t) = [\beta 1 + (\alpha-\beta)cc] \cdot \omega \quad (13)$$

Thus $$\omega = [\beta 1 + (\alpha-\beta)cc]^{-1} \cdot L_0 f(t) \quad (14a)$$

$$= (1/\alpha\beta)[\alpha 1 - (\alpha-\beta)cc] \cdot L_0 f(t) \quad (14b)$$

$$= (1/\alpha\beta)[\alpha L_0 - (\alpha-\beta)L_0 \cdot cc] f(t) \quad (14c)$$

It follows that $$\omega \times c = [f(t)/\beta] L_0 \times c = dc/dt \quad (15)$$

which implies a precession of c(t) about the constant direction of $L_0$. It also implies that $L_0 \cdot c(t)$ is constant, equal to $L_0 \cdot c_0$, where $c_0$ is the initial value of c(t) and is random.

Equation 15 can be solved for c(t), the motion of the crystal, as given by Equation 16. Letting z denote the unit vector along the constant vector $L_0$, $$c(t) = zz \cdot c_0 + \cos \Phi(t)[c_0 - zz \cdot c_0] + \sin \Phi(t) z \times c_0 \quad (16a)$$

where $$d\Phi(t)/dt = L_0 f(t)/\beta \quad (16b)$$

Thus, the time dependence of $\Phi$ is given by Equation 17a through 17e.

$$\Phi(t) = \Phi_0\{(1+\xi)\cos\theta + (1-\xi)\sin\theta \Delta\omega t - \cos(\Delta\omega t-\theta) - \xi\cos(\Sigma\omega t+\theta)\} \quad (17a)$$

where $$\Phi_0 = \tfrac{1}{2}\mu_0 V \Delta\chi |H_{01} \times H_{02}|/\beta(\Delta\omega)^2 \quad (17b)$$

$$\Delta\chi = \chi_1 - \chi_2 \quad (17c)$$

$$\Delta\omega = \omega_1 - \omega_2 \quad (17d)$$

$$\Sigma\omega = \omega_1 + \omega_2 \quad (17e)$$

Finally, the angular velocity is given by Equation 18.

$$\omega(t) = (1/\alpha\beta)[\alpha L_0 - (\alpha-\beta)L_0 \cdot c_0 c(t)] f(t) \quad (18)$$

Equation 16 for the motion of the unit vector c(t) shows the desired continuous rotation of the crystal, modified by a superimposed oscillation, under the action of the dual magnetic fields $H_1$ and $H_2$.

In some embodiments, one of the frequencies is zero, so that one of the fields is constant in time. The above analysis applies, with $\omega_2=0$.

In some embodiments, more than one susceptibility is involved in the process by relying on sufficient variation of susceptibility with frequency in the vicinity of an operating frequency and taking advantage of the finite linewidth of any realistic source of the magnetic field. For a narrowband signal as the magnetic field, corresponding to a slow modulation of a sinusoidal carrier, the field is given by Equation 19.

$$H(t) = H_p(t)\cos\omega_0 t + H_q(t)\sin\omega_0 t \quad (19)$$

where $H_p(t)$ and $H_q(t)$ are the in-phase and quadrature components of the slowly-varying amplitude of the carrier oscillation at frequency $\omega_0$, comprising the narrow linewidth of the source field. In this case, the short-term time-averaged torque is given by Equation 20.

$$M(t) \times H(t) = \tfrac{1}{2}[d\chi(\omega_0)/d\omega] d[H_p(t) \times H_q(t)]/dt \quad (20)$$

The analysis then follows the one shown above, with $d\chi/d\omega$ essentially replacing $\Delta\chi/\Delta\omega$.

2.3. Anisotropic Susceptibility.

In some embodiments, anisotropic magnetic susceptibility is relied upon to produce torque. Assuming anisotropy of the magnetic susceptibility of the hemozoin crystal, as suggested by its crystalline structure and as reported in the literature, the desirable dual susceptibility can be brought into play by relying on its distinct values in the magnetic susceptibility tensor. For purposes of illustration, it is assumed that the crystal has a uni-axial structure (like structure 211 or structure 212). If the anisotropy should turn out to be biaxial instead (e.g., like structure 213), the analysis is quite similar but more complicated.

With a longitudinal and a transverse susceptibility, the magnetic susceptibility tensor $\chi$ is expressed by Equation 21.

$$\chi = \chi_c cc + \chi_x(1-cc) = \chi_x 1 + (\chi_c-\chi_x)cc \quad (21)$$

Substituting into Equation 4, yields Equations 22a through 22c.

$$T = \mu_o V M(t) \times H(t) = \mu_o V[\chi H(t)] \times H(t) \quad (22a)$$

$$= \mu_o V[\chi_x H(t) + (\chi_c-\chi_x) cc \cdot H(t)] \times H(t) \quad (22b)$$

$$= \mu_o V(\chi_c-\chi_x) c \cdot H(t) c \times H(t) \quad (22c)$$

The vacuum permeability $\mu_o$ is used because the smallness of the susceptibility makes the crystal's permeability essentially the vacuum value for the integration. It is evident that there will be no torque if there is no anisotropy (because no anisotropy means that $\chi_c=\chi_x$).

It is noted that the needed dual susceptibility is built into the susceptibility tensor in this embodiment. Consequently, even a single unidirectional oscillating magnetic field, e.g., of the form $H=H_o \cos\omega_o t\, z$, applied along the z-axis will engender a torque in the anisotropic crystal.

The response of the crystal to the applied torque is given by the equation of motion expressed in Equation 23a through 23c.

$$T = dL/dt \quad (23a)$$

where $$L = J \cdot \omega \quad (23b)$$

and $$dc/dt = \omega \times c \quad (23c)$$

L is the angular momentum and ω is the angular velocity vector of the crystal. Equation 23c governs the precession of the crystal as a rigid body. The equations are valid in the laboratory's inertial system where the external magnetic field H is applied. Substituting yields Equation 24.

$$T = dL/dt = J_x d\omega/dt + (J_c - J_x)[d(c \cdot \omega)/dtc + c \cdot \omega dc/dt] \quad (24)$$

It is easily verified that c·w is a constant of the motion and, as the crystal is assumed to be at rest initially, we have c·ω=0 for all t. The equation of motion therefore reduces to Equation 25.

$$T = J_x d\omega/dt \quad (25)$$

Which leads to Equation 26a, or 26b and 26c, $$d\omega/dt = [\mu_o V(\chi_c - \chi_x)/J_x] c \cdot H c \times H \quad (26a)$$

$$d\omega/dt = \Omega_o^2 \cos^2 \omega_o t c \cdot z c \times z \quad (26b)$$

$$\Omega_o^2 = \mu_o V(\chi_c - \chi_x) H_o^2 / J_x \quad (26c)$$

and Equation 27.

$$dc/dt = \omega \times c \quad (27)$$

In terms of the angle θ between c and z at time t, the equations of motion are given by Equations 28a through 28c.

$$d\omega/dt = \Omega_o^2 \cos^2 \omega_o t \cos \theta \sin \theta \quad (28a)$$

and $$\omega = -d\theta/dt \quad (28b)$$

or $$d^2\theta/dt^2 = -\Omega_o^2 \cos^2 \omega_o t \cos \theta \sin \theta \quad (28c)$$

The initial conditions are $\theta(0) = \theta_o$ and $d\theta(0)/dt = 0$. If the factor, $\cos^2 \omega_o t$, were absent, Equation 28c would be the equation of motion for a pendulum. If the time scales of the magnetic field's oscillation and the natural precession frequency are very different, an approximate solution is easily obtained. For example, if $\omega_o \ll \Omega_o$, an approximate solution to the modified pendulum equation is Equation 29a through 29b.

$$\sin \theta(t) = k sn([\Omega_o/\omega_o] \sin \omega_o t + K(k), k) \quad (29a)$$

where $$k = \sin \theta_o \quad (29b)$$

The function sn(x, k) is the Jacobian elliptic sine function with modulus k and K(k) is the complete elliptic integral of the first kind.

This solution exhibits oscillation but not a full rotation. Full revolution requires two magnetic fields, as shown above. This oscillation without rotation is not expected to be as effective in disrupting the parasite as rotation alone, or oscillation with rotations. Thus use of a single oscillating magnetic field, as disclosed by Feagan et al., does not obtain the synergistic results of applying two different oscillating magnetic fields simultaneously.

A single rotating field, comprised of two orthogonal field components in time quadrature (both using the same frequency with a quarter-cycle phase difference) can be used, provided there is anisotropy to furnish distinct values of the susceptibility for these two field components at the same frequency.

2.4. Combined Torque

In some embodiments, mechanical excitation of the paramagnetic structure relies on both the spectral dispersion of the susceptibility (its variation with frequency) and its inherent anisotropy (the dependence of the susceptibility on the direction of the applied magnetic field). The response is a combination of the precession and oscillation exhibited by the solutions presented above. An example of the combined torque embodiment is described in more detail below.

2.5. Rotating Magnetic Field

In some embodiments, a rotating magnetic field is imposed. The rotating magnetic field is achieved by superimposing two sinusoidally varying linear magnetic fields that are 90 degrees out of phase and of the same strength but oscillating in perpendicular directions. In some embodiments, the field strengths are not equal. Those fields are generated by two perpendicularly-oriented pairs of coils that carry sinusoidal currents, temporally 90 degrees out of phase and oscillating at the desired rotation frequency. It was found that there is sufficient anisotropy of the crystal to allow use of the same frequency for the two oscillating fields that are oriented perpendicular to each other and still have two magnetic susceptibilities at play.

It has also been determined, on the basis of theoretical calculations and then confirmed by experiments, that there is a maximum frequency that can be used, for a given strength of a rotating magnetic field, to achieve complete sustained rotation of the target hemozoin crystal, which depends on the environment of the crystal. The maximum rotation frequency, ωmax, varies as the square of the magnetic field amplitude, H, and depends on the following properties of the crystal and its environment: size of crystal; tensor moment of inertia of crystal; magnetic susceptibility of crystal; anisotropy of tensor magnetic susceptibility of crystal; viscosity of fluid in vacuole; and viscosity of fluid around the host cell. The magnetic field frequency ω for complete sustained rotation of the target hemozoin crystal is given in Equation 30.

$$\omega \leq \omega max \quad (30a)$$

$$\omega max = \tfrac{1}{2} \mu_0 V(\chi_c - \chi_x) H^2 (R_0 + R)/R_0 R \quad (30b)$$

where R and $R_0$ are viscosity coefficients related to the crystal in the cell, and related to the entire cell in the environment of the cell, respectively. At higher frequencies, the viscosity of the environment prevents the crystal from making a full rotation relative to the host cell within the period of the oscillation. For hemozoin crystals in malaria parasites in infected red blood cells, ωmax is about 10 Hz for the magnetic field strength of about 15 Gauss that was used and in the experimental environment that applied. The ωmax is expected to be different for other field strengths and in vivo.

3. Apparatus and Method

Figure 4:
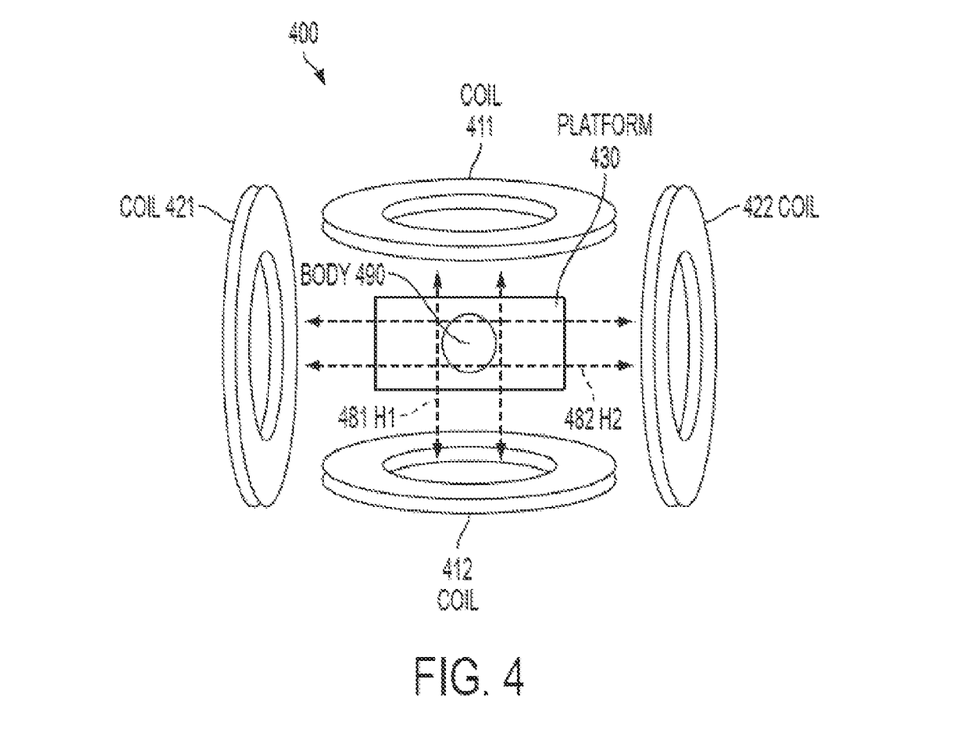
FIG. 4 is a block diagram that illustrates an example apparatus according to an embodiment.

FIG. 4 is a block diagram that illustrates an example apparatus 400 according to an embodiment. For example, looking down on a plan view, the apparatus 400 includes two magnets and a platform 430 for a body 490, such as the body of a patient. The illustrated embodiment includes a first magnet, comprised of coil 411 and coil 412, adapted to generate a first magnetic field H1 481 oscillating at a first frequency in a first direction. Also included is a second magnet, comprised of coil 421 and coil 422, adapted to generate a second magnetic field H2 oscillating at a second frequency in a different second direction. The patient treatment platform 430 is adapted to position a body 490, e.g. a patient, simultaneously in the first magnetic field H1 and the second magnetic field H2. In some embodiments, the second frequency is different from the first frequency.

In the illustrated embodiment, the first frequency and the second frequency are selected so that magnetic susceptibility for microscopic paramagnetic structures associated with a condition in the body is different in the first magnetic field than in the second magnetic field.

According to a method embodiment, two magnetic fields H1 and H2 are applied to a body 490 simultaneously. The first frequency and the second frequency are selected so that magnetic susceptibility for microscopic paramagnetic structures associated with a condition in the body 490 is different at the first frequency than at the second frequency.

In some embodiments, the body 490 is not the body of a patient with a disease condition, but, instead, is some other vessel that includes microscopic paramagnetic structures, such as a machine with such structures included for microscopic polishing or other microscopic machining tasks.

In some embodiments, the microscopic paramagnetic structures are artificially manufactured and introduced into the body, for example, to treat solid cancer tumors.

4. Example Embodiments

An embodiment was performed as an experiment at Columbia University, conducted Oct. 15, 2008. This embodiment has verified the above theoretical approach and has resulted in statistically significant destruction of the malaria parasite by application of magnetic fields.

The experiment used two pairs of parallel air-core coils of the Helmholtz type, roughly 15 cm in diameter and separated by about 15 cm. It is noted that there is no need for the high degree of field uniformity that is obtainable when the coil radius precisely equals the coil separation, for a true Helmholtz coil configuration. The two pairs of coils were oriented at right angles to each other and excited by currents from two separate sources at two slightly different frequencies.

The experiment used an alternating current (AC) at a first frequency (e.g., 1021 Hz) with a magnetic field strength of Gauss root means square (rms) generated by one pair of coils and another AC current, from a separate source, at a second frequency (e.g., 1016 Hz) with a magnetic field strength of Gauss rms generated by the other pair of coils. Note that there is no need for the magnetic fields to be highly uniform, as the target crystals are orders of magnitude smaller than the spatial scale of variation of the fields. There is also no need to make the two fields coherent, because there is no need to generate a smoothly rotating magnetic field, so they were not derived from a single source but rather from two separate power sources. A sample of malaria-infected red blood cells (RBC) at the trophosoite/schizont stage (when there is significant amount of hemozoin present) was suspended at the intersection of these two perpendicular magnetic fields and exposed to the simultaneous oscillating magnetic fields for a treatment duration (e.g., 30 minutes).

Figure 5:
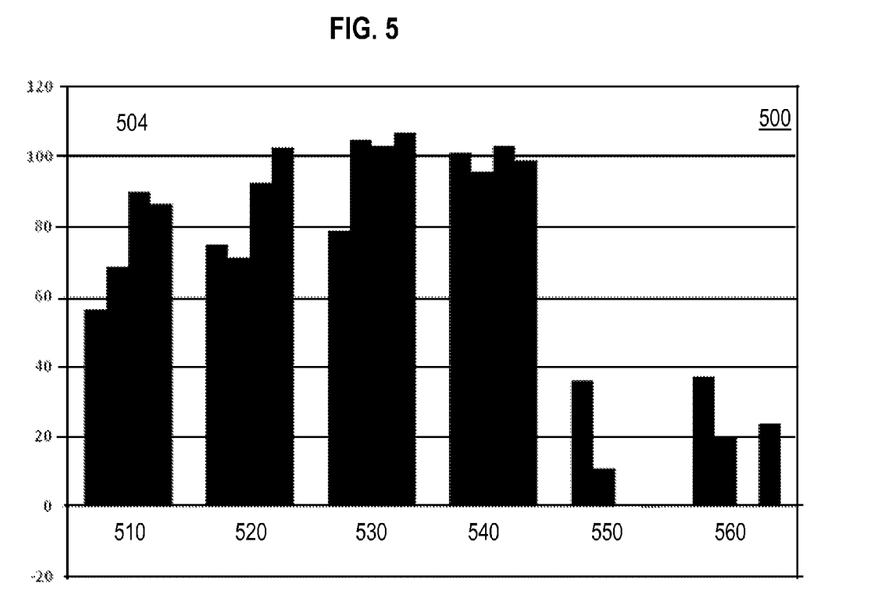
FIG. 5 is a graph that illustrates results of applying a method to ameliorate malaria, according to an embodiment.

FIG. 5 is a graph 500 that illustrates results of applying a method to ameliorate malaria, according to various embodiments. The vertical axis indicates percent of malaria parasites observed in a sample relative to a control sample that was not subjected to any treatment. Parasite observations were measured using dsDNA binding fluorochrome SYBR Green I (SG-I) from Invitrogen, Carlsbad, Calif. SG-I is a fluorescent dye based on cyanine which is similar to ethidium iodide and binds to double stranded DNA (as an intercalator) and broadly used for quantitative PCR, flow cytometry, DNA electrophoresis etc. Upon binding to dsDNA it absorbs in 488 nm (blue) and emits in 522 nm (green). It is used to quantify the malaria parasite's DNA which correlates with parasite's viability. This approach seems to be more accurate than the direct count of parasite. The units are percent (%) of SYBR staining compared to staining in untreated control (100%). The samples comprised malaria-infected red blood cells (RBC) with ~5% parasitemia, and ~90% schizont stage.

The horizontal axis separates different groupings of observations. Each group is presented with 4 columns, which correspond respectively to days 1, 2, 3 and 4 after the treatment.

The first group 510 represents samples that were treated with perpendicular simultaneous magnetic fields at 1021 and 1016 Hz for 30 minutes. Note that kill rates (survival rates about 55%) achieved in 30 minutes are comparable to the effects of Feagan et al. treatment with a single field for 24 hours, a time advantage factor of about 50. On the basis of the theory outlined above, the difference frequency of 5 Hz was the fundamental frequency of the induced precession of the hemozoin crystals in the malaria sample.

The second group 520 represents samples that were treated with perpendicular simultaneous magnetic fields at 1021 and 1016 Hz for 30 minutes, followed by perpendicular simultaneous magnetic fields at 100 and 105 Hz for 30 minutes.

The third group 530 represents samples that were treated with perpendicular simultaneous magnetic fields at 100 and 105 Hz for 30 minutes, followed by perpendicular simultaneous magnetic fields at 10 and 15 Hz for 30 minutes.

The fourth group 540 represents samples that were treated with perpendicular simultaneous magnetic fields at 10 and 15 Hz for 60 minutes.

The fifth group 550 and sixth group 560 were established as negative controls to represent high kill rates using other mechanisms that are not suitable for treating living human patients. Group 550 represents samples that were treated with short ultraviolet (UV) electromagnetic radiation at a distance of 20 centimeters (cm, $1\ cm=10^{-2}$ meters) for a duration of 30 minutes. Group 560 represents samples that were treated by heating to 50 degrees Celsius for a duration of 30 minutes.

It looks like higher frequency causes statistically significant damage to the parasite, as seen in groups 510 and 520. In group 510 the parasite never recovered to the control levels (even on day 4 it was 90% of control). Days 1 and 2 in both groups 510 and 520 showed an impressive (definitely statistically significant) drop in dsDNA (to around 60-70%) which means there was an impaired replication. Group 510 parameters for the experiment used an AC current at 1021 Hz with a magnetic field strength of Gauss rms generated by one pair of coils and another AC current, from a separate source, at 1016 Hz with a magnetic field strength of Gauss rms generated by the other pair of coils.

The parasite seems to be more sturdy than expected because group 560 (50 degrees Celsius for 30 minutes) failed to eliminate it entirely. UV treatment in group 550 seems to be more effective as a negative control.

In another set of experiments, magnetic fields were applied for durations on the order of the malaria parasite cycle, to ensure all infected RBCs were treated at times of maximum vulnerability. The results show unpredicted large improvement over prior approaches.

Figure 6:
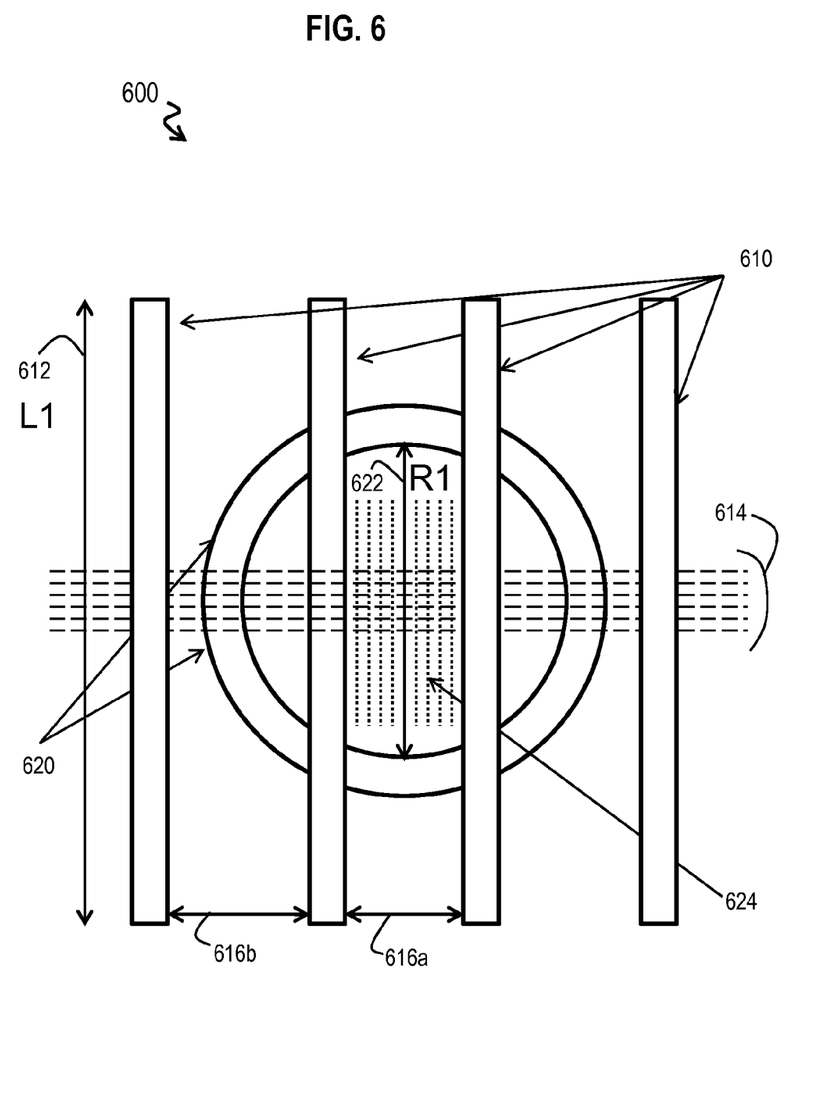
FIG. 6 is a block diagram that illustrates an example experimental apparatus, according to an embodiment.

FIG. 6 is a block diagram that illustrates an example experimental apparatus 600, according to another embodiment. In this planar view looking down from the top of the apparatus, four large Merritt coils 610 with L1 outer diameter 612 are deployed in parallel vertical planes and connected in series. The inner two coils are 610 are separated by a first distance 616a and the outer coils are separated from the adjacent inner coil by a second distance 616b. In the experimental example, the L1 outer diameter 612 is 230 millimeters (m, 1 mm=$10^{-3}$ meters), the first distance 616a is 40 mm and the second distance 616b is 60 mm. The direction of magnetic field 614 generated by the 4 large Merritt coils 610 is indicated by dashed lines.

Two smaller Helmholtz coils 620 with R1 inner diameter 622 are deployed orthogonally to the coils 610 in parallel horizontal planes and connected in series. The two coils 620 (view of a bottom coil is blocked by the top coil) are separated by a distance (not shown). In the experimental example, the R1 inner diameter 622 is 135 millimeters, and the two Helmholtz coils are separated by distance of about 65 mm. The direction of magnetic field 624 generated by the two small Helmholtz coils 620 is perpendicular to the planar view and indicated by dots. In some experiments the large Merritt coils 610 were driven at frequencies up to about 25 Hz, and the small Helmholtz coils 620 were driven a frequencies up to 20 Hz. In some embodiments, both sets of coils 610, 620 were driven at the same frequency but out of phase temporally by 90 degrees to induce a rotating magnetic field.

Figure 7:
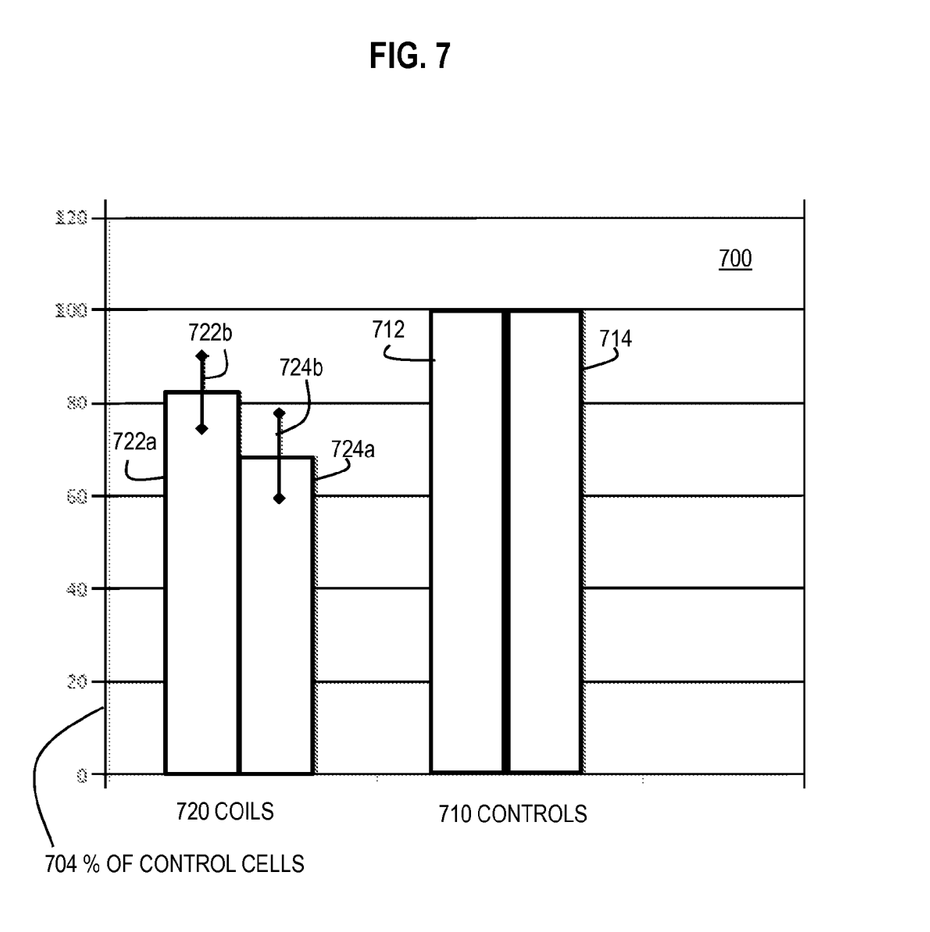
FIG. 7 is a bar graph that illustrates results of applying a single magnetic field to diseased cells.

FIG. 7 is a bar graph 700 that illustrates results of applying a single magnetic field to diseased cells, as suggested by Feagan et al., with similar results. The vertical axis 704 indicates percent of parasite DNA contents of a control sample with malaria parasites not subjected to magnetic fields, and incubated at 37° Celsius for 48 hours, based on SYBR staining. The parasite DNA content is 100% of the control content after 48 hours by definition, as shown by control bar 714. The control sample content is also 100% after 24 hours as shown by control bar 712.

Test samples with malaria parasite were subjected to a single orientation 5 Hz oscillating magnetic field of strength 15 Gauss for 24 hours, shown as coils bar 722a, or for 48 hours, shown as coils bar 724a. Bar 722a shows the reduction in viability of the parasite to about 80% after 24 hours' exposure; and bar 724a shows the reduction in viability of the parasite to about 70% after 48 hours' exposure. The standard error ranges 722b and 724b for bars 722a and 724a, respectively, indicate that the differences from control levels are highly significant for both. The chance that the difference is random is less than $1.6\times10^{-12}$ for bar 722a and less that $9.7\times10^{-7}$ for bar 724a. Similar percentages were observed by Feagan et al.

Figure 8A:
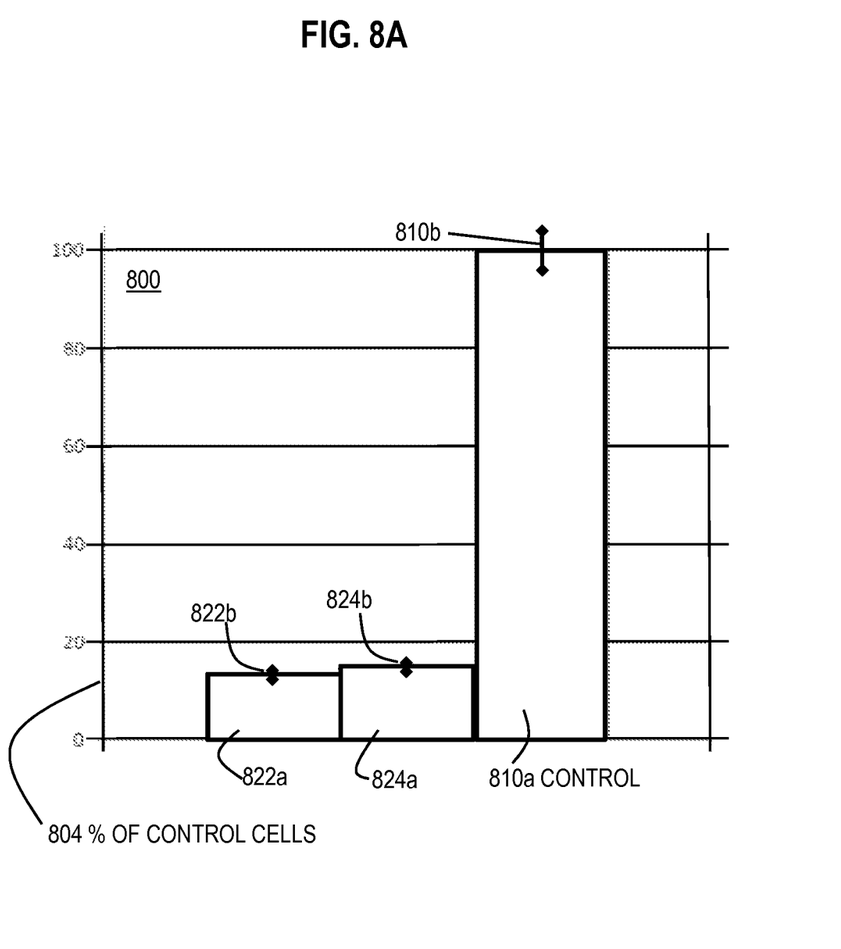
FIG. 8A through FIG. 8C are bar graphs that illustrate benefits of applying dual magnetic fields to diseased cells, according to various embodiments.
Figure 8B:
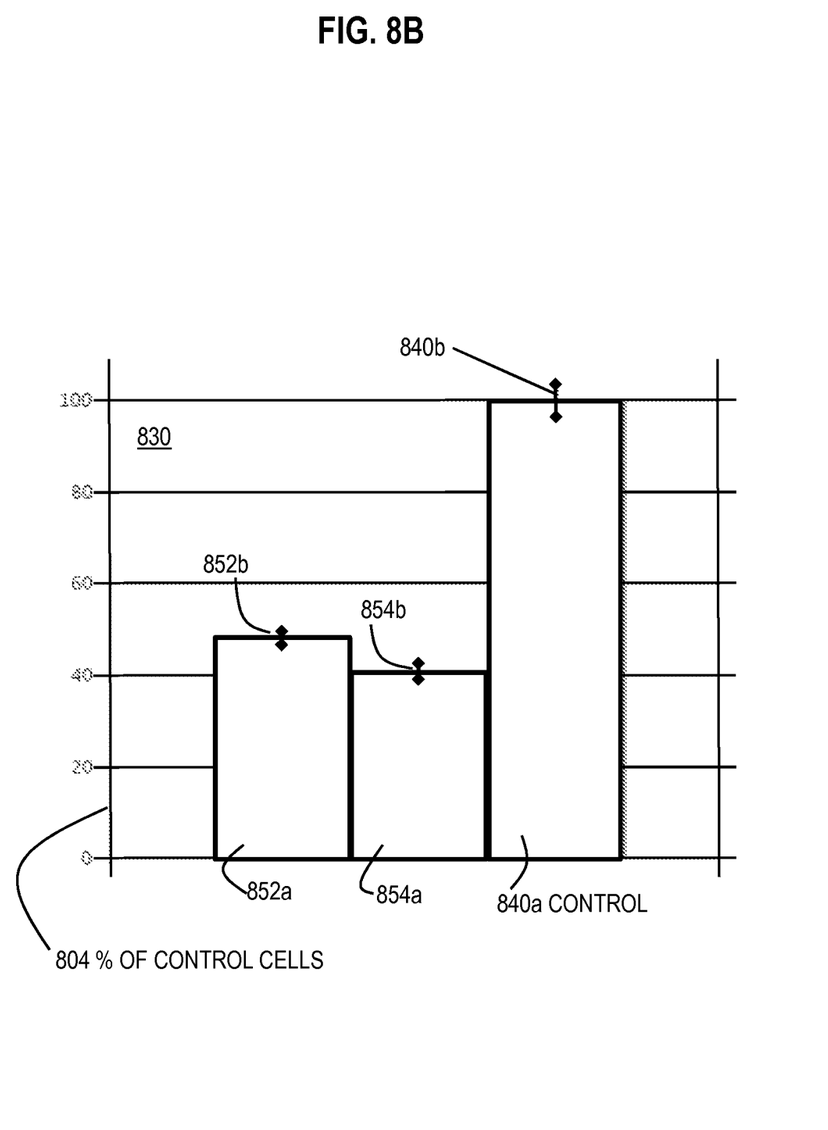
Figure 8C:
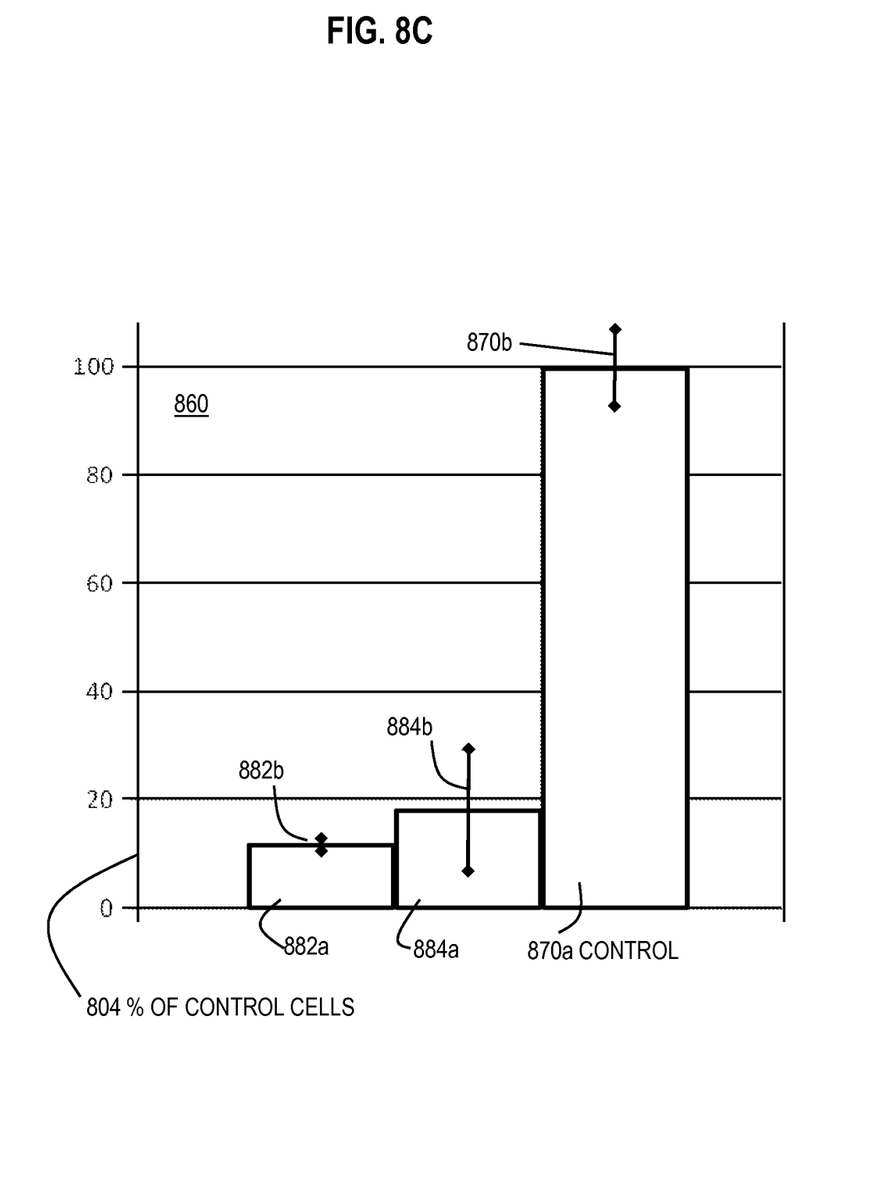

FIG. 8A through FIG. 8C are bar graphs that illustrate benefits of applying dual magnetic fields to diseased cells, according to various embodiments. The vertical axis 804 indicates percent of parasite DNA contents of a control sample with malaria parasites not subjected to magnetic fields, and incubated at 37° Celsius for 48 hours, based on SYBR staining. In FIG. 8A, the starting cultures comprise 200 microliters (μl, 1 μl=$10^{-6}$ liters) including 3% Hermatocrit (HC) with 1% parasitemia of which 90% are in ring stage. Hematocrit is the percent of the volume of packed RBC in the mixture, e.g., the HC of whole blood is about 45-60%. In the illustrated embodiments, 3% HC means, that if the culture is spun in a centrifuge, 3% of the volume of the culture media will be taken by packed RBC. After 24 hours the culture was diluted 1:2 with fresh 3% HC. The 48 hour endpoint was measured using SYBR staining for parasite DNA.

There were two sets of samples: 24-hour samples were exposed to magnetic fields for 24 hours and then for another 24 hours without magnetic fields. The 48-hour samples were exposed to oscillating magnetic fields for the entire 48 hours. This way the samples could be collected together and the effects measured together. In this regard, it was possible that 24-hour samples could have undergone some parasite population rebound, but not much rebound was observed, indicating persistent therapeutic effects.

Test samples with malaria parasite were subjected to magnetic fields of strength 15 Gauss oscillating at two different frequencies, 10 Hz and 8 Hz, using both sets of coils depicted in FIG. 6. Merritt coils (610) were driven at 8 Hz, while Helmholtz coils (620) were driven at 10 Hz. In bar graph 800 of FIG. 8A, the control samples are shown as bar 810a, which is 100% by definition, with standard error 810b. The 24-hour samples results are shown as bar 822a; and the 48-hour samples results are shown as bar 824a. The standard error ranges 822b and 824b for bars 822a and 824a, respectively, indicate that the differences from control levels are highly significant for both. The chance that the difference is random is less than $1\times10^{-6}$ for both. This experiment shows close to 90% reduction in parasite's viability under the double field magnetic irradiations at low frequencies—substantially and surprisingly better than results from a single oscillating magnetic field. The results for 48 hours are essentially the same as the results for 24 hours, indicating little benefit provided by the additional 24 hours of exposure.

The results are better than a single magnetic field, but less favorable at frequencies above the maximum frequency, ωmax, which is about 10 Hz in malaria parasite infected RBC for the magnetic field strength that was used and in the experimental environment that applied, as shown in graph 830 of FIG. 8B. Vertical axis 804 is as described above. In FIG. 8B, the malaria samples were prepared a bit differently. The starting cultures comprise 200 μl including 3% HC with 2% parasitemia of which 90% are in ring stage. After 24 hours the culture was not diluted with fresh 3% HC. The 24-hour samples were exposed to magnetic fields for 24 hours and then for another 24 hours incubated without magnetic fields.

Test samples with malaria parasite were subjected to magnetic fields of strength 12 Gauss oscillating at two different frequencies, 10 Hz and 14 Hz, using both sets of coils. When different frequencies were used, the pattern was always the same, the Merritt coils 610 were driven at a lower frequency than were the Helmholtz coils 620. Thus, in the illustrated experiment, the Merritt coils 610 were driven at 10 Hz and the Helmholtz coils 620 were driven at 14 Hz. In bar graph 830 of FIG. 8B, the control samples are shown as bar 840a, which is 100% by definition, with standard error 840b. The 24-hour samples results are shown as bar 852a; and the 48-hour samples results are shown as bar 854a. The standard error ranges 852b and 854b for bars 852a and 854a, respectively, indicate that the differences from control levels are highly significant for both. The chance that the difference is random is less than $1\times10^{-6}$ for both. This experiment shows the reduction in parasite's viability to 50% and 40% in 24 and 48 hours, respectively, under double field magnetic irradiation. The results for 48 hours are significantly better than the results for 24 hours, indicating less than a full kill after 24 hours of exposure, and some benefit to continuing in dual oscillating magnetic fields to 48 hours.

The results are very favorable for a rotating magnetic field as shown in graph 860 of FIG. 8C. Vertical axis 804 is as described above. In FIG. 8C, the malaria samples were prepared as described for FIG. 8B. The 24-hour samples were exposed to magnetic fields for 24 hours and then for another 24 hours incubated without magnetic fields.

Test samples with malaria parasite were subjected to a rotating magnetic field of strength 20 Gauss oscillating at 4.7 Hz for 24 hours, using both sets of coils 610 and 620, with one set shifted by 90 degrees relative to the other. During the second 24 hours for the 48 hour samples, a rotating magnetic field of strength 15 Gauss oscillating at 9.4 Hz, using both sets of coils, with one set shifted by 90 degrees relative to the other. At both frequencies, the Helmholtz coils 620 were driven with a sine function of time having the given frequency while Merritt coils 610 were driven with a cosine function of time having the given frequency. In bar graph 860 of FIG. 8B, the control samples are shown as bar 870a, which is 100% by definition, with standard error 870b. The 24-hour samples results are shown as bar 882a; and the 48-hour samples results are shown as bar 884a. The standard error ranges 882b and 884b for bars 882a and 884a, respectively, indicate that the differences from control levels are highly significant for both. The chance that the difference is random is less than $1\times10^{-6}$ for both. This experiment shows the reduction in parasite's viability down to 10% and 20% in 24 and 48 hours, respectively. The higher relative viability after 48 hours is possibly explained by an increase in number of parasite cells which passed the schizont stage and a probably less efficient irradiation regimen than during first 24 hours.

The parameters quoted here are not to be interpreted as anything but representative of what is possible to implement some embodiments of the invention. Other frequencies, other frequency differences, other field strengths, and other exposure regimens may also be effective, to a greater or lesser degree, than those used in this particular embodiment of the invention. Routine experimentation should find a range of effective parameter values. Sources of magnetic fields other than the air-core coils used in this experiment may also serve the purpose as well or better than those used in the example embodiment.

5. Extensions and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for treating conditions in a body, comprising:
    treating a body which contains therein a plurality of microscopic paramagnetic structures for which magnetic susceptibility to a first magnetic field oscillating at a first frequency in a first direction is different from magnetic susceptibility to a different second magnetic field oscillating at a different second frequency in a different second direction;
    applying torque to said microscopic paramagnetic structures by exposing said body simultaneously to a first magnetic field oscillating at a first frequency in a first direction and a different second magnetic field oscillating at a different second frequency in a different second direction;
    exciting said microscopic paramagnetic structures into mechanical motion by said torque applied in response to the first magnetic field oscillation at a first frequency in a first direction and the different second magnetic field oscillating at a different second frequency in a different second direction.

2. A method as recited in claim 1, wherein at least one of the first frequency and the second frequency is greater than 100 Hz.

3. A method as recited in claim 2, wherein each of the first frequency and the second frequency is greater than 100 Hz.

4. A method as recited in claim 1, wherein a difference between the first frequency and the second frequency is less than about 100 Hz.

5. A method as recited in claim 1, wherein the second magnetic field is temporally 90 degrees out of phase with the first magnetic field.

6. A method as recited in claim 1, wherein the first frequency and second frequency are each less than about 15 Hertz.

7. A method for ameliorating a symptom of a disease in an animal comprising:
    treating said animal for which a disease or diseased cells selectively include a plurality of microscopic paramagnetic structures for which magnetic susceptibility to a first magnetic field oscillating at a first frequency in a first direction is different from magnetic susceptibility to a different second magnetic field oscillating at a different second frequency in a different second direction;
    exposing said animal to a therapeutically effective strength and duration of a first magnetic field oscillating at a first frequency in a first direction and, simultaneously, a different second magnetic field oscillating at a different second frequency in a different second direction;
    exciting said microscopic paramagnetic structures into mechanical motion by the torque applied in response to the first magnetic field oscillating at a first frequency in a first direction and the different second magnetic field oscillating at a different second frequency in a different second direction.

8. A method as recited in claim 7, wherein the disease is a parasite.

9. A method as recited in claim 7, wherein the diseased cells are a stage of a malaria parasite.

10. A method as recited in claim 7, wherein at least one of the first frequency and the second frequency is greater than 100 Hz.

11. A method as recited in claim 10, wherein each of the first frequency and the second frequency is greater than 100 Hz.

12. A method as recited in claim 7, wherein a difference between the first frequency and the second frequency is less than about 100 Hz.

13. A method as recited in claim 7, wherein the second magnetic field is temporally 90 degrees out of phase with the first magnetic field.

14. A method as recited in claim 7, wherein the first frequency and second frequency are each less than about 15 Hertz.

* * * * *